United States Patent [19]

Burton

[11] Patent Number: 4,912,155

[45] Date of Patent: Mar. 27, 1990

[54] ANTIOXIDANT AROMATIC FLUOROPHOSPHITES

[75] Inventor: Lester P. J. Burton, Baton Rouge, La.

[73] Assignee: Ethyl Corporation, Richmond, Va.

[21] Appl. No.: 20,023

[22] Filed: Feb. 27, 1987

[51] Int. Cl.$^4$ .................... C08L 23/32; C07F 9/146
[52] U.S. Cl. ........................ 524/118; 558/84; 558/195; 524/121; 524/149
[58] Field of Search .................. 558/84, 195; 524/118, 524/121, 149

[56] References Cited

U.S. PATENT DOCUMENTS 4,094,855 6/1978 Spivack ........................ 558/195
4,233,207 11/1980 Spivack ........................ 558/195

Primary Examiner—Anton H. Sutto
Attorney, Agent, or Firm—Joseph D. Odenweller

[57] ABSTRACT

Organic materials normally subject to gradual degradation in the presence of oxygen are stabilized by inclusion of an aromatic fluorophosphite having at least one benzene group bonded through oxygen to phosphorus and at least one fluorine atom bonded directly to the same phosphorus. Stabilization is improved by also including a conventional phenolic antioxidant. Many of the aromatic fluorophosphites are new compounds.

42 Claims, No Drawings

ANTIOXIDANT AROMATIC FLUOROPHOSPHITES

BACKGROUND OF THE INVENTION

1. Field of the Invention

This invention relates to aromatic fluorophosphorus compounds and their use as antioxidants in organic materials such as organic polymers.

2. Description of the Prior Art

Phosphites, phosphonites and other organic phosphorus compounds are used in organic polymers and other organic materials as antioxidants. They are generally considered better than phenolic antioxidants at high temperatures because they eliminate hydroperoxides which decompose and lead to autooxidation chain reactions. Thus, phosphorus compounds are important for oxidative stability during various operations including polyolefin extrusion.

Phenolic and phosphorus antioxidants are often used together in polyolefin homopolymers and copolymers to provide antioxidant protection for both low and high temperature exposure. Unfortunately, additional expense is encountered as additives in larger amounts are needed for the polymers. Thus, there exists a need for effective antioxidants at a reasonable additive price, not only for polyolefins, but other substrates as well.

It is common practice to include an antioxidant in organic materials normally susceptible to oxidative degradation. Many of the antioxidants employed have limited effectiveness or tend to impart undesirable properties to the organic material such as causing color. The problem is particularly acute with polymers and copolymers of ethylenically unsaturated monomers, especially polyolefins such as polypropylene. These materials are subjected to elevated temperatures during processing, which tends to destroy many antioxidants with the result that the polymer rapidly degenerates during use. The aromatic fluorophosphorus compounds of the present invention allow organic materials to maintain excellent color and thermal stability.

SUMMARY OF THE INVENTION

According to the present invention, certain aromatic fluorophosphorus compounds are provided which are very effective as stabilizers in a wide range of organic materials. The aromatic fluorophosphorus compounds are very effective because they retard changes in viscosity of organic materials stabilized therewith for extensive periods of time under processing conditions. In addition, they are stable when stored at room temperatures. They are especially effective when used in combination with phenolic antioxidants.

DESCRIPTION OF THE PREFERRED EMBODIMENTS

A preferred embodiment of the present invention is an organic material normally susceptible to gradual oxidative degradation when in contact with oxygen said organic material containing an antioxidant amount of an aromatic fluorophosphorus compound being characterized by having at least one benzene group bonded through oxygen to a trivalent phosphorus atom and at leas one fluorine atom bonded to the same phosphorus atom.

Any organo phosphorus compound meeting the above definition is readily recognize by its structural formula. One highly preferred class of such compounds can be represented by the formula:

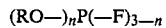

Formula I wherein R is a substitute or unsubstituted aryl group wherein the substituents are selected from alkyl, aryl, aralkyl, cycloalkyl, hydroxy, alkoxy, aryloxy, halo, alkoxycarbonyl, alkoxycarbonylalkyl an acyloxy and n is 1 or 2. In a still more preferred embodiment of this class of compounds the substituents are alkyls having 1-carbon atoms, aryls having 6-12 carbon atoms, arylalkyls having 7-12 carbon atoms, cycloalkyls having 5-8 carbon atoms, hydroxy, alkoxy having 1-12 carbon atoms, aryloxy having 6-12 carbon atoms, halo, alkoxycarbonylalkyl having 1-20 carbon atoms in its alkoxy moiety and 1-3 carbon atoms in its alkyl moiety, alkoxy carbonyl having 1-20 carbon atoms in its alkoxy moiety and acyloxy having 1-4 carbon atoms.

Representative examples of the above substitutents are methyl, isopropyl, sec-butyl, tert-butyl, n-decyl, sec-dodecyl, sec-eicosyl, phenyl, o-tolyl, p-tolyl, naphthyl, 4-phenylphenyl, 4-sec-hexylphenyl, benzyl, alpha-methylbenzyl, phenethyl, 4-tert-butylbenzyl, 4-tert-butyl-alpha-methylbenzyl, cyclopentyl, cyclohexyl, cyclooctyl, methoxy, ethoxy, isopropoxy, 2-ethylhexoxy, 2-ethoxyethoxy, isobutoxy, dodecoxy, phenoxy, 4-ethylphenoxy, napthoxy, 4-phenylphenoxy, chloro, bromo, fluoro, iodo, methoxycarbonylmethyl, butoxycarbonylethyl, dodecyloxycarbonylpropyl, octadecyloxycarbonylethyl, icosyloxycarbonylethyl, methoxycarbonyl, butoxycarbonyl, decyloxycarbonyl, octadecyloxycarbonyl, icosyloxycarbonyl, formate, acetyloxy, propionyloxy, butyryloxy and the like.

Representative examples of the group (RO) include phenoxy, 2-methyl-6-tert-butylphenoxy, 2,4-di-tert-butylphenoxy, 2,6-diisopropylphenoxy, 2,4-diisopropllphenoxy, 2,6-di-secbutylphenoxy, 4-phenylphenoxy, 2-(alpha-methylbenzyl)phenoxy 2,6-di(alpha-methylbenzyl)phenoxy, 2-cyclohexylphenoxy, 2-methyl-4-cyclohexylphenoxy, 4-hydroxyphenoxy, 4-methoxyphenoxy, 2-ethoxyphenoxy, 4-dodecyloxyphenoxy,4-phenoxyphenoxy, 4-octadecyloxycarbonylethyl-2,6-di-tert-butylphenoxy, -dodecyloxycarbonylpropyl, 4-acetyloxyphenoxy and the like.

Some representative compounds of Formula I are: bis(2, 6-di-tert-butylphenyl) fluorophosphite; 2,6-di-tert-butylphenyl difluorophosphite; bis(2,4-di-tert-butylphenyl) fluorophosphite; 2,4-di-tert-butylphenyl difluorophosphite; bis(4-(2-octadecyloxycarbonylethyl)-2,6-di-tert-butylphenyl) fluorophosphite; (aka bis[2,6-di-tert-butyl-4-(2-carbooctadecyloxyethyl)phenyl]fluorophosphite); 4-(2-octadecyloxycarbonylethyl)-2,6-di-tertbutylphenyl difluorophosphite; bis(4-(2-dodecyloxycarbonylethyl)-2,6-di-sec-butylphenyl) fluorophosphite and the like.

The most preferred compounds in Formula I are: bis(2,6-di-tert-butylphenyl) fluorophosphite: bis(2,4-di-tert-butylphenyl) fluorophosphite and bis(4-(2-octadecyloxycarbonylethyl)-2,6-di-tert-butylphenyl) fluorophosphite.

A second highly preferred class of compounds of the invention are the cyclic fluorophosphites having the structure

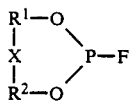

Formula II wherein R¹ and R² are substituted or unsubstituted aryl groups wherein the substituents are selected from alkyl, aryl, aralkyl, cycloalkyl, hydroxy, alkoxy, aryloxy and halo, and X is selected from the group consisting of a single bond connecting R¹ and R² and divalent bridging groups selected from divalent aliphatic hydrocarbons containing 1-12 carbon atoms, —O— and —$S_q$ wherein q is an integer from 1 to 3.

In a still more preferred embodiment of the cyclic fluorophosphite of Formula II, the substituent groups on R¹ and R² are alkyls having 1-20 carbon atoms, aryls having 6-12 carbon atoms, aralkyls having 7-12 carbon atoms, cycloalkyls having 5-8 carbon atoms, hydroxy, alkoxy having 1-12 carbon atoms, aryloxy having 6-12 carbon atoms and halo, and X is selected from the group consisting of a single bond connecting R¹ and R² and divalent bridging groups selected from divalent aliphatic hydrocarbons containing 1-12 carbon atoms, —O— and —$S_q$ wherein q is an integer from 1 to 3. Examples of the resulting —R¹—X—R²— groups are 2,2'-bis(4,6-di-tert-butylphenyl); 2,2'-bis(4-chloro-6-isopropylphenyl): 2,2'-bis(4-methoxy-6-tert-pentylphenyl); 2,2'-methylenebis(4,6-di-tert-butylphenyl); 2,2'-ethylidenebis(4,6-di-tert-butylphenyl); 4,6,-di-tertbutyl-4,-methyl-6-isopropyl-2,2'-isopropylidenebisphenyl; 2,2'thiobis(4-methyl-6-tert-butylphenyl); 2,2'-trithiobis(4,6-di-tert-butylphenyl); 2,2'-thiobis(4-methoxy-6-tert-butylphenyl); 2,2'-dithiobis(4-methyl-6(alpha-methylbenzyl)phenyl).

A third highly preferred embodiment is represented by the structure:

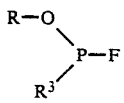

Formula III wherein R is a substituted or unsubstituted aryl group wherein the substituents are selected from alkyl, aryl, aralkyl, cycloalkyl, hydroxy, alkoxy, aryloxy, halo, alkoxycarbonyl, alkoxycarbonylalkyl and acyloxy and R³ is selected from the group consisting of alkyl, cycloalkyl, aralkyl, aryl, substituted aryl, alkoxy, cycloalkoxy, aryloxy and aralkoxy radicals.

The preferred R of substituents are alkyls having 1-20 carbon atoms, cycloalkyls have 5-8 carbon atoms, aryls having 6-12 carbon atoms, aralkyls having 7-12 carbon atoms, hydroxy, alkoxy having 1-12 carbon atoms, aryloxy having 6-12 carbon atoms, halo, alkoxycarbonylalkyl having 1-20 carbon atoms on its alkoxy moiety and 1-3 carbon atoms on its alkyl moiety, alkoxycarbonyl having 1-20 carbon atoms in its alkoxy moiety and cyloxys having 1-4 carbon atoms. R³'s more preferably selected from alkyls having 1-20 carbon atoms, cycloalkyls having 5-8 carbon atoms and arylalkyls having 7-12 carbon atoms which are bonded through oxygen to phosphorus and aryls having 6-12 carbon atoms, alkyls having 1-20 carbon atoms, cycloalkyls having 5-8 carbon atoms and arylalkyls having 7-12 carbon atoms which are bonded directly to phosphorus.

Representative examples of R—O — in formula III are the same set forth for this same group under structure I.

Representative examples of R³ in formula III are methoxy, sec-butoxy, decoxy, 2-ethyldecoxy, octadecoxy, eicosoxy, cyclopentoxy, cyclohexoxy, cyclooctoxy, phenoxy, 2,6-di-tertbutylphenoxy, 2,4-di-tert-butylphenoxy, 2-tert-butyl-4methylphenoxy, 4-methoxyphenoxy, benzyloxy, 4-ethylbenzyloxy, phenyl, p-tolyl, 4-phenylphenyl, methy, ethyl, butyl, dodecyl, octadecyl, eicosyl, cyclohexyl, cyclooctyl, benzyl, 4-ethyl-alpha-methylbenzyl and the like.

Typical compounds of structure III are methyl phenyl fluorophosphite, dodecyl 2,6-di-tert-butylphenyl fluorophosphite, eicosyl 2,4-di-tert-butylphenyl fluorophosphite, cyclohexyl 2,6-di-tert-butyl-4-ethoxyphenyl fluorophosphite, diphenyl fluorophosphite, bis(2,6-di-tert-butylphenyl) fluorophosphite, bis(2,4-di-tert-butylphenyl) fluorophosphite, bis(2,4-di-tert-pentylphenyl) fluorophosphite, benzyl 2(alpha-methylbenzyl)-4-chlorophenyl fluorophosphite, phenyl 2-methyl-6-tert-butyl-4-phenoxyphenyl fluorophosphite, 2,4-di-tert-butylphenyl methylfluorophosphonite, 2,6-di-tert-butyl-4-methylphenyl benzylfluorophosphonite, 2,6-di-tert-butyl-4-methoxyphenyl eicosylfluorophosphonite and the like.

A fourth class of fluorophosphorus compounds of the invention are represented by the structure:

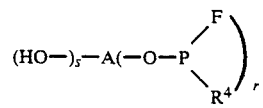

Formula IV wherein A is a mono- or poly-nuclear aromatic group, R⁴ is independently selected from fluorine, aryloxy, alkaryloxy, alkoxy and polyalkoxy and r is an integer from 1 to 4, s is an integer from 0 to 3 and (r+s) equals the valence of A.

Representative examples of R⁴ in formula IV are fluorine, phenoxy, 4-ethylphenoxy, 2-ethyl-4-isobutylphenoxy, napthoxy, 2-tert-butylphenoxy, 2,6-di-tert-butylphenoxy, 2-methyl-6-tert-butylphenoxy, 2,4-di-tert-butylphenoxy, 2,6-di-sec-butylphenoxy, 2,6-di-tert-butyl-4-methylphenoxy, 4-dodecylphenoxy, 4-(alpha-methylbenzyl)phenoxy, methoxy, ethoxy, butoxy, decyloxy, dodecyloxy, eicosyloxy, 2-ethoxyethoxy, 2butoxyethoxy and the like.

"A" in Formula IV can be any of a broad range of organo groups as long as it contains at least one benzene ring in its structure. "A" can contain 4 or more benzene rings. "A" is generally but not necessarily a hydrocarbon. "A" may also contain oxygen and/or nitrogen.

The group "A" of the more important types of structure for compounds IV fall in the following sub-classes.

Sub-class IV (i) A groups have the structure:

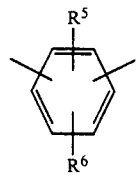

wherein R⁵ and R⁶ are hydrogen or alkyls having 1-12 carbon atoms. Representative examples of these divalent phenylene groups are 1,4-phenylene, 1,2-phenylene, 2,6-di-tert-butyl-1,4-phenylene, 2,5-di-tert-butyl-1,4-phenylene, 2-methyl-5-dodecyl-1, 4-phenylene and the like.

Representative examples of fluorophosphorus compounds containing the "A" group IV (i) are 2,5-di-tert-butyl-1,4-phenylene bis(difluorophosphite); 2,5-tert-butyl-1,4-phenylene bis(phenyl fluorophosphite); 3,5-di-tert-butyl-4-hydroxyphenyl difluorophosphite; 2,5-di-tert-butyl-4-hydroxyphenyl octadecyl fluorophosphite; 2,4-di-tert-butylphenyl 2-(alpha-methylbenzyl)-4-hydroxyphenyl fluorophosphite; 2,6-di-tert-butylphenyl 2-methyl-4-hydroxy-5-tert-butylphenyl fluorophosphite; 2-dodecyl-4-hydroxy-5-methylphenyl dodecyl fluorophosphite; 2,5-di-tert-butyl-1,4-phenylene bis(2,6-di-tert-butylphenyl fluorophosphite) and the like.

Sub-class IV (ii) A groups have the structure:

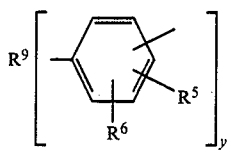

wherein $R^5$ and $R^6$ are as before, $R^9$ is an aliphatic hydrocarbon radical having 1 to 6 carbon atoms and having valence y and y is an integer from 2 to 3.

Representative compounds of sub-class IV (ii) are:[1]

[1] "T" represents a tert-butyl group

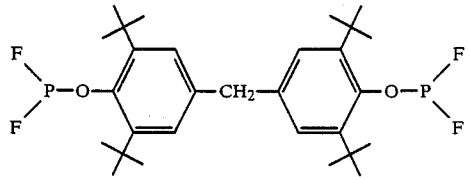

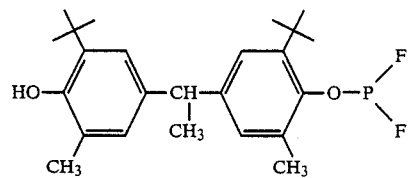

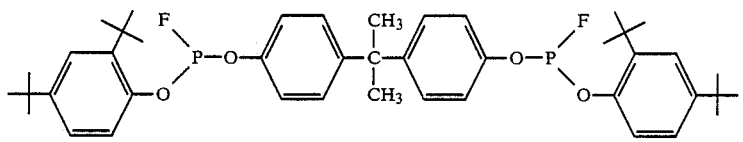

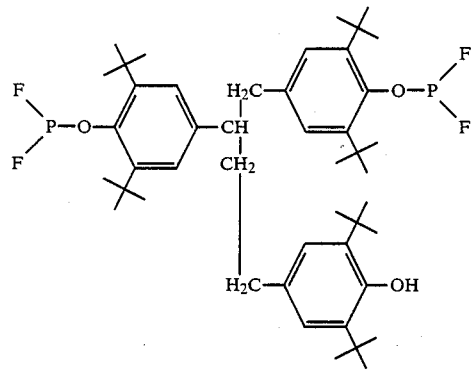

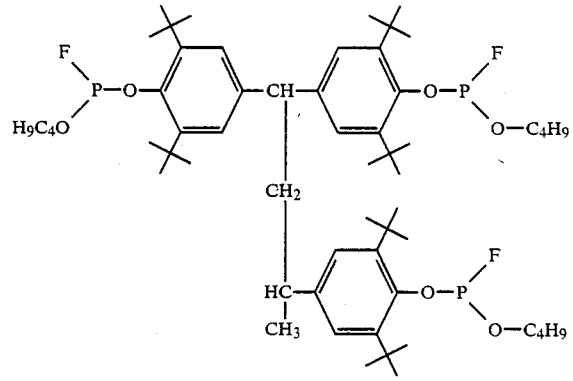

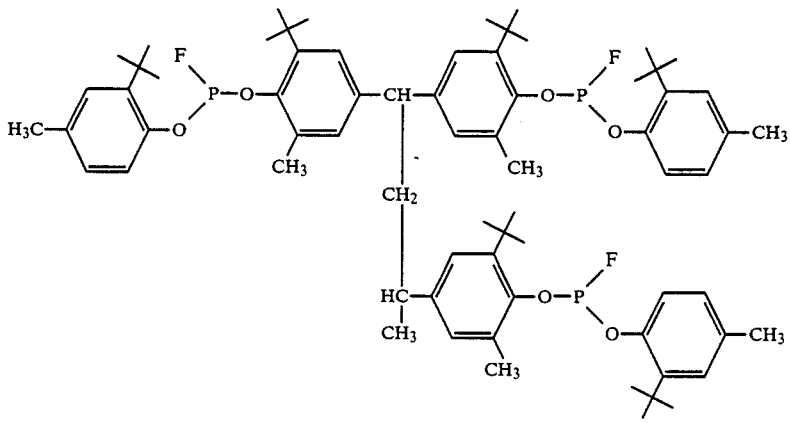

Sub-class IV (iii) A groups have the structure:

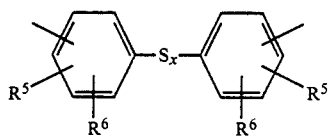

wherein $R^5$ and $R^6$ are as before and x is an integer from 1 to 3. Representative examples of structure IV (iii) A groups are: 4,4'-thiobis(2-methyl-6-tert-butylphenyl), 4,4'-thiobis(2,6-di-tert-butylphenyl), 4,4'-dithiobis(2,6-di-tert-butylphenyl), 22,-dithiobis(4-methyl-6-tert-butylphenyl), 2,2'thiobis(4-tert-butylphenyl) and the like.

Representative examples of organo fluorophosphorus compounds of formula IV containing sub-class IV (iii) A groups are: 4,4'thiobis(2-methyl-6-tert-butylphenyl diflurophosphite), 4,4'-thiobis(2-ethyl-6-tert-butylphenyl butyl fluorophosphite), 4,4'-thiobis(2,6-di-tert-butylphenyl difluorophosphite), 4,4'-dithiobis(2,6-di-tert-pentylphenyl phenyl fluorophosphite) and the like.

Sub-class IV (iv) A groups have the structure:

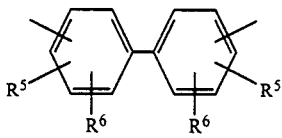

wherein $R^5$ and $R^6$ are as before. Examples of these biphenyl groups are

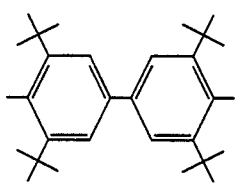

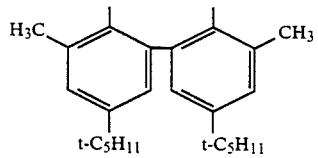

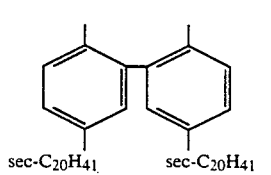

Representative examples of formula IV organo fluorophosphorus compounds of sub-class IV (iv) are:

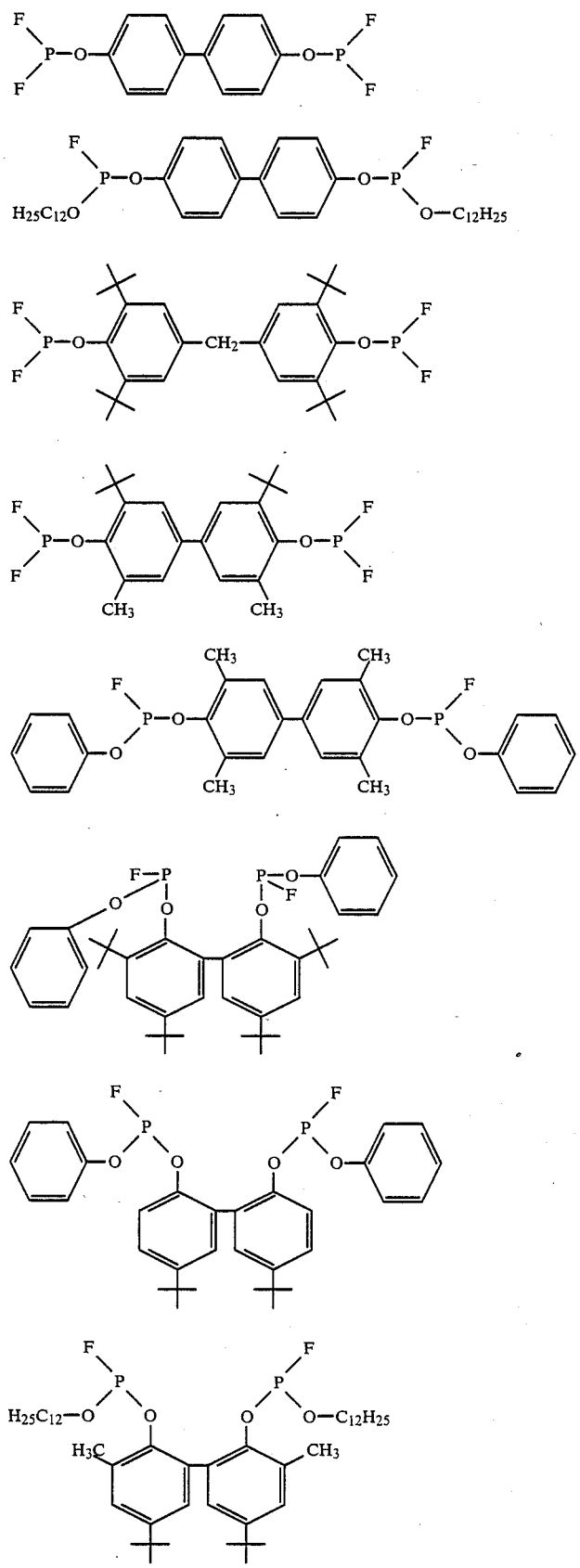
Sub-class IV (v) A groups have the structure:

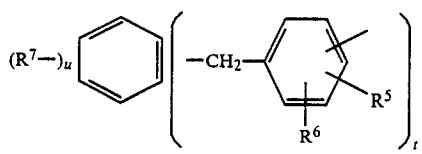

wherein $R^5$ and $R^6$ are as before, $R^7$ is hydrogen or an alkyl having 1–6 carbon atoms, t is an integer from 2 to 3, u is an integer from 0 to 4 and (t+u) equals 2 to 6.

Representative examples of organo fluorophosphorus compounds of Formula IV having a sub-class IV (v) A group are: tris(difluorophosphite ester) of 1,3,5-trimethyl-2,4,6-tris (3,5-di-tert-butyl-4-hydroxybenzyl)benzene; tris(phenyl fluorophosphite ester) of 1,3,5-trimethyl-2,4,6-tris[3,5 di-tert-butyl-4-hydroxybenzyl]benzene; tris(n-dodecyl fluorophosphite ester) of 1,3,5-trimethyl-2,4,6-tris (3,5-di-tert-butyl-4-hydroxybenzyl)benzene; bis (2-tert-butylphenyl fluorophosphite ester) of 2,3,5,6-tetramethyl-1,4-bis-[3,5-di-tert-butyl-4-hydroxybenzyl]-benzene; bis(n-octyl fluorophosphite ester) of 2,3,5,6-tetraethyl 1,4-bis(3,5-ditert-butyl-4-hydroxybenzyl)benzene; tris(2,6-di-tert-butyl-4-methylphenyl fluorophosphite ester) of 1,3,5-tris(3-methyl-5-tert-butyl-4-hydroxybenzyl]benzene; bis(2,6-di-tertbutylphenyl fluorophosphite ester) of 1,4-bis[3,5-di-tert-butyl-4hydroxybenzyl]benzene; tris(2,6-di-tert-butyl-4-ethylphenyl fluorophosphite ester) of 2,4,6-triethyl-1,3,5-tris[2-methyl-6-tert-butyl-4-hydroxybenzyl]benzene and the like.

Sub-class IV (vi) A groups have the structure:

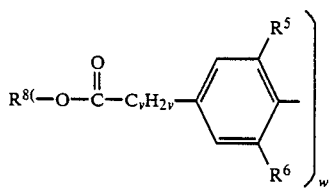

wherein $R^5$ and $R^6$ are as before, $R^8$ is an aliphatic hydrocarbon radical having 1–30 carbon atoms and having valence w, w is an integer from 1 to 4 and v is an integer from 0 to 4.

Representative examples of organo fluorophosphorus compounds of Formula IV having sub-class IV (vi) A groups are: 2-methyl-6-tert-butyl-4(methoxycarbonylmethyl)phenyl difluorophosphite; 2,6-di-tert-butyl-4(dodecyloxycarbonyl)phenyl 2,6-di-tert-butyl-4-methylphenyl fluorophosphite; 2,6-i-tert-butyl-4-(octadecyloxycarbonylethyl)phenyl difluorophosphite; 2,6-di-tert-butyl-4-(octadecyloxycarbonylethyl)phenyl 2,4-di-tert-butylphenyl fluorophosphite; 2,6-di-tert-butyl-4-(octadecyloxycarbonylethyl)phenyl n-decyl fluorophosphite; 2,6-di-tert-butyl-4-(octadecyloxycarbonylethyl)phenyl 2,6-di-tert-butylphenyl fluorophosphite; 2,6-di-tert-pentyl-4-(octadecyloxycarbonylethyl) phenyl 2-tert-pentylphenyl fluorophosphite; 2-methyl-6-tert- butyl-4-(docosyloxycarbonylmethyl)phenyl 2,6-di-tert-pentylphenyl fluorophosphite; tetrakis(difluorophosphite ester) of tetrakis(methylene 3-(3,5-di-tert-butyl-4-hydroxyphenyl) propionate)methane; tetrakis(2,4-ii-tert-butylphenyl fluorophosphite ester) of tetrakis(methylene 3-(3,5-di-tert- butyl-4-hydroxyphenyl)propionate)methane; tetrakis(2,4-di-ter- thexylphenyl fluorophosphite ester)of tetrakis(methylene 2-(3-tert-pentyl-4-hydroxyphenyl)acetate)methane tris (difluorophosphite ester) of trimethylolpropanetris [3-(3,5-di-tert-butyl-4-hydroxy-phenyl)proponiate], tris(3-methyl5-tert-butylphenyl fluorophosphite ester) of trimethylol ethanetris[3-methyl-5-tert-butyl-4-hydroxybenzoate] and the like.

Sub-class IV (vii) A groups have the structure:

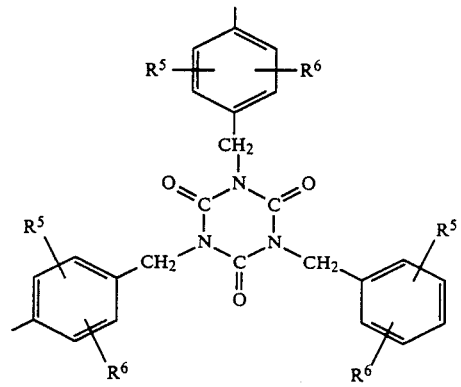

wherein $R^5$ and $R^6$ are the same as before.

Typical organo fluorophosphorus compounds of formula IV having a sub-class IV (vii) A group are:
tris(difluorophosphite ester) of 1,3,5-tris (3,5-di-tert-butyl-4-hydroxybenzyl)isocyanurate; tris(2,4-di-tert-butylphenyl fluorophosphite ester) of (3,5-di-tert-butyl-4-hydroxybenzyl)isocyanurate; tris(2,6-di-tert-butyl-phenyl fluorophosphite ester) of 1,3,5-tris (3,5-di-tert-butyl-4-hydroxybenzyl)isocyanurate; tris(methyl fluorophosphite ester) of 1,3,5-tris(3,5-di-tert-butyl-4-hydroxybenzyl)isocyanurate; tris(n-dodecyl fluorophosphite ester) of tris(4-hydroxybenzyl)isocyanurate and the like.

Sub-class IV (viii) A group have the structure:

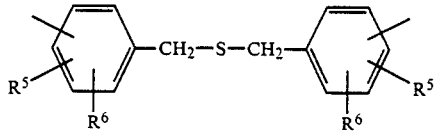

wherein $R^5$ and $R^6$ are as before.

Typical organo fluorophosphorus compounds of Formula IV having a sub-class IV (viii) A groups are:

Difluorophosphite diester of alpha,alpha'-thiobis (2,6-di-tert-butyl-p-cresol); 2,4-di-tert-butylphenyl fluorophosphite diester of 4-hydroxybenzyl 3,5-di-tert-butyl-4-hydroxybenzyl sulfide; dodecyl fluorophosphite diester of bis(3,5-di- tert-butyl-4-hydroxybenzyl)sulfide; difluorophosphite diester of bis-(3-methyl-5-tert-butyl-4-hydroxybenzyl)sulfide; 2,6-di-tert-butylphenyl fluorophosphite diester of bis-(3,5-didodecyl-4hydroxybenzyl)sulfide; phenyl fluorophosphite diester of bis-(3,5-di-isopropyl-4-hydroxybenzyl)sulfide and the like.

The preferred aromatic fluorophosphites of the present invention are bis(2,4-di-t-butylphenyl) fluorophosphite, 2,2'-ethylidenebis(4,6-di-t-butylphenyl) fluorophosphite and 2,2'-bis(2,6-di-tert-butylphenyl) fluorophosphite.

The aromatic fluorophosphites of the invention are particularly useful as antioxidants. The antioxidants can be used in a broad range of organic material normally subject to gradual degradation in the presence of oxygen during use over an extended period. In other words, the organic materials protected by the present antioxidants are of the type in which the art recognizes the need for antioxidant protection and to which an antioxidant of some type is customarily added to obtain an extended service life The oxidative degradation protected against is the deterioration of the organic composition during or after processing rather than, for example, combustion.

Examples of organic materials in which the antioxidants of this invention are useful include polymers, both homopolymers and copolymers, of olefinically unsaturated monomers, for example, polyolefins such as polyethylene, polypropylene, polybutylene and the like.

Also, polyaalohydrocarbons such as polyvinyl chloride, polychloroprene, polyvinylidene chloride, polyfluoroolefins, and the like, are afforded stabilization. The antioxidants provide antioxidant protection in natural and synthetic rubbers such as copolymers of olefinically unsaturated monomers including styrene butadiene rubber (SBR rubber), ethylene-propylene copolymers, ethylene-propylene-diene terpolymers such as the terpolymer of ethylene, propylene and cyclopentadiene or 1,4-cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise, acrylonitrile-butadiene-styrene (ABS) resins are effectively stabilized. Ethylene-vinyl acetate copolymers (EVA) are protected, as are butene-methylacrylate copolymers. Nitrogen-containing polymers such as polyurethanes, nitrile rubber, and lauryl acrylate-vinyl pyrrolidone copolymers are effectively stabilized. Adhesive compositions such as solutions of polychloroprene (neoprene) in toluene are protected. Polyphenylene ethers such as poly-2,6-dimethyl-1,4-phenylene ethers either alone or in combination with blending agents such synthetic rubbers are protected by the present invention. Likewise polystyrene and rubber modified polystyrene (i.e. high impact polystyrene) are stabilized.

Petroleum oils such as solvent-refined, midcontinent lubricating oil and Gulf Coast lubricating oils are effectively stabilized. In hydrocarbon lubricating oils, both mineral and synthetic, the present antioxidants are effective when used in combination with a zinc dihydrocarbyl dithiophosphate e.g. zinc dialkyl dithiophosphate or zinc dialkaryl dithiophosphate.

Synthetic ester lubricants such as those used in turbines and turbojet engines are given a high degree of stabilization. Typical synthetic ester lubricants include di-2-ethylhexyl sebacate, trimethylolpropane tripelargonate $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethylene glycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenyl using a copper-pyridine catalyst are stabilized. Polycarbonate plastics and polyformaldehydes are also protected.

Linear polyesters such as phthalic anhydride-glycol condensates, poly[ethylene terephthalate] (PET), and poly[butylene terephthalate] (PBT), are given a high degree of protection. Other polyesters such as trimellitic acid-glycerol condensates are also protected. Polyacrylates such as polymethylacrylate and polymethylmethacrylate are effectively stabilized. Polyacrylonitriles an copolymers of acrylonitriles with other olefinically unsaturated monomers such as methylmethacrylates are also effectively stabilized.

The antioxidants of the present invention are preferably used in either thermoset or thermoplastic polymer compositions. The thermoset polymers are those plastics which when subjected to heat, will normally become infusible or insoluble and as such cannot be remelted. They have elaborately cross-linked three dimensional structures and are used for plastics, elastomers, coatings and adhesives.

In contrast to the thermoset polymers, most thermoplastic polymers can be made to soften and take a new shape by the application of heat and pressure. Thermoplastic polymers comprise long-chain molecules often without any branching (e.g., high density polyethylene). Thermoplastic polymers normally are rigid at operating temperatures, but can be remelted and reprocessed. They include polyethylene, polycarbonate, polypropylene, polystyrene, polyvinyl chloride, acrylonitrile-butadiene-styrene (ABS), nylon, and the like, including polymers intended for high temperature applications. The most preferred organic compounds intended for the practice of the present invention are polypropylene and polyethylene.

The more preferred utility of the new additives is in the stabilization of thermoplastic polymers during processing such as during extrusion. Of these the most preferred polymers are polyethylene, polypropylene, linear low density polyethylene and polycarbonates.

The antioxidants of the present invention are useful to control oxidative and color degradation of resins used as tackifiers in adhesives. The resin which can be protected include synthetic hydrocarbon resins, such as cycloaliphatic $C_5$ resins, aromatic $C_9$ resins, terpene resins and the like. Also included are natural resins, such as wood rosin, gum rosin and toll oil rosin which are processed for tackifier applications.

The antioxidants are incorporated into the organic material in a small but effective amount so as to provide the required antioxdant protection. A useful range is generally from about 0.005 to about 5 weight percent of organic material, and a preferred range is from about 0.01 to 2 weight percent.

Methods of incorporating the antioxidants into the organic material are well known. For example, if the material is liquid, the additive can be merely mixed into the material. Solid organic materials can be merely sprayed with a solution of the additive in a volatile solvent. For example, stabilized grain products result from spraying the grain with a toluene solution of the antioxidant. In the case of rubbery polymers, the additive the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

The fluorophosphites of the present invention are readily made by reacting the appropriate phenolic compound with phosphorus trichlorideoor phosphorus tribromide to form an aryloxy mono- or di-halo (e.g., Cl or Br) phosphite. This in turn is reacted with a fluorinated compound such as HF, LiF, NaF, KF, RbF, CsF, SbF$_3$, SbF$_5$, AgF, HgF$_2$, CoF$_3$,SF$_4$ and the like which exchange F for C$_1$ or Br bonded to phosphorus.

In making compounds of Formula I-IV, a phenol is reacted with PCl$_3$ or PBr$_3$ to form a chloro or bromophosphite intermediate which is then reacted with a fluorinating agent as shown in the following equations.

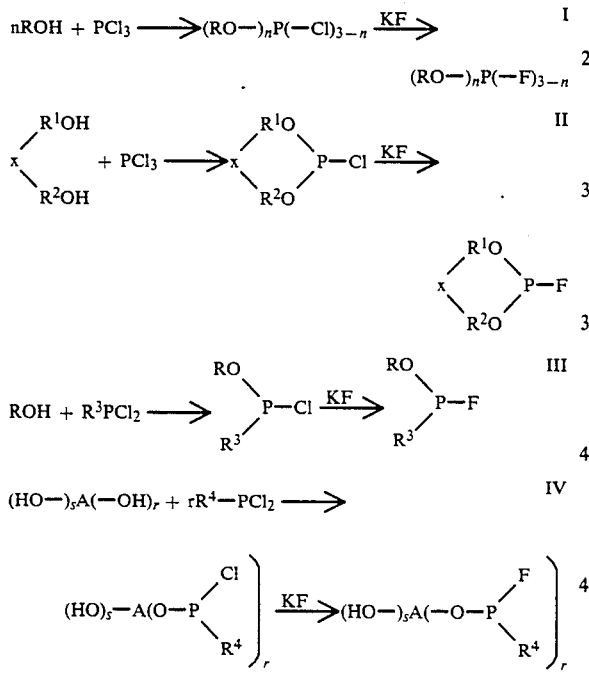

In the above illustration, PCl$_3$ is used but PBr$_3$ could also be used. Likewise, KF is used as the fluorinating agent but any of the other fluorinating agents could be used in its place.

The amount of PCl$_3$ or PBr$_3$ used to form the intermediate chloro or bromophosphite depends on the number of hydroxyl groups in the phenolic reactant and the average number of residual P-Cl or P-Br groups desired in the intermediate. For example, if one mole of PCl$_3$ is reacted with one mole of a monohydroxy phenolic compound the average intermediate will be a dichlorophosphite. Likewise if two moles of a monohydroxy phenolic compound are reacted with one mole of PCl$_3$ the average intermediate compound will be a monochlorophosphite. When one mole of an ortho-ortho bridged diphenol is reacted with one mole of PCl$_3$, the major component in the intermediate will be a cyclic monochlorophosphite such as may be used to make a fluorophosphite of Formula II.

The starting phenolic compounds are well known and described in the literature such as in U.S. Pat. No. 2,836,577; U. S. Pat. No. 944,986; U.S. Pat. No. 3,562,338; U.S. Pat. No. 1,972,599; U.S. Pat. No. 2,807,653; U.S. Pat. No. 3,4494441; U.S. 1,892,990; U.S. Pat. No. 2,394,754; U. S. 2,479,948; U.S. Pat. No. 2,905,674; U.S. Pat. No. 3,367,980; U.S. Pat. No. 3,069,384; U.S. Pat. No. 2,202,877; U.S. Pat. No. 2,313,782; U.S. Pat. No. 3,065,275; U.S. Pat. No. 2,84,619; U.S. Pat. No. 2,315,556; U.S. Pat. No. 2,469,469; U.S. Pat. No. 2,836,609; U.S. Pat. No. 3,146,273; U.S. Pat. No. 2,008,032; U.S. Pat. No. 2,714,120; U.S. Pat. No. 3,093,587; U.S. Pat. No. 3,0601121; U.S. 2,538,355; U.S. Pat. No. 2,364,338; U.S. Pat. No. 3,330,859; U.S. Pat. No. 3,062,896; U.S. Pat. No. 3,026,64; U.S. Pat. No. 3,531,483; J. A. Chem. Soc. 78 1069 (1956) and others.

The reaction of the PCl$_3$ or PBr$_3$ with the phenol is preferably conducted in an aprotic solvent such as THF, benzene, toluene, xylene, heptane, octane, cyclohexane and the like. The reaction can also be conducted in an excess of PCl$_3$ or PBr$_3$ which functions as a solvent or reaction medium. The reaction temperature should be high enough to cause the reaction to proceed at a reasonable rae but not so high as to cause decomposition. A useful temperature range is from $-30°$ to $300°$ C. A preferred temperature range is 0–100° C. and a more referred temperature range is about 25–75° C. and must preferably at reflux temperature.

The chloro or bromophosphite intermediate is fluorinated by reaction with at least an equivalent amount of the fluorinating agent based o the equivalent of Cl and/or Br bound to phosphorus. An excess can be used. The fluorination is preferably conducted in a aprotic solvent. The reaction can be conducted in the same reaction mixture resulting from the preparation of the intermediate.

The fluorination temperature should be high enough to cause the fluorine to replace the chlorine or bromine but not so high as to cause decomposition. A useful temperature range is about 10–300° C., more preferably 20–150° C. and most preferably at reflux.

The aromatic fluorophosphites of the present invention may be used alone as the antioxidant or may be used in combination with phenolic antioxidants, thioesters such as dilauryl thiodipropionate and distearyl thiodipropionate, light stabilizers such as hindered amines or ultraviolet light absorbers, metal deactivators, pigments, dyes, lubricants such as calcium stearate, nucleation agents and talc and other fillers.

Some representative examples of useful UV stabilizers are:

| UV Stabilizers |
| --- |
| Nickel dibutyldithiocarbamate |
| 2-hydroxy-4-n-octyloxybenzophenone |
| 2,4-di-tert-butylphenyl 3,5-di-tert-butyl-4-hydrozybenzoate |
| Nickel bis[o-ethyl(3,5-di-tert-butyl-4-hydroxybenzyl) phosphonate |
| 2-(3',5'-di-tert-butyl-2'-hydroxyphenyl-5-chlorobenzotriazole |
| Bis(2,2,6,6-tetramethyl-piperridinyl-4)sebacate |
| Bis(1,2,2,6,6-pentamethyl-piperridinyl-4)sebacate |
| n-Butyl-(3,5-di-tert-butyl-4-hydroxybenzyl)-bis(1,2,2,6,6-pentamethyl-4-piperridinyl)malonate |
| Dimethyl succinate polymer with 2,2,6,6-tetramethyl-1-piperridineethanol |
| N,N'-bis(2,2,6,6-tetramethyl-4-piperridinyl)-1,6-hexane diamine, polymer with 2,4,6-trichloro-1,3,5- |

| UV Stabilizers |
| --- |
| triazine and 2,4,4-trimethyl-1,2-pentanamine |
| polymeric hindered amines such as Gasorb UV3346 |
| (American Cyanamid); Spinuvex A-36 (Montedison); |
| Chimassorb 944 (Ciba-Geigy) |
| 2-(2'-hydroxy-3',5'-di-tert-amylphenyl)benztriazole |
| 2,2'-thiobis(4-tert-octylphenolato)butylamino-Nickel(II) |
| Nickel bis((ethyl-(3,5-di-tert-butyl-4-hydroxybenzyl)- |
| phosphonate) |
| and the like. |

Phenolic antioxidants which are suitable for use in the present invention are well known in the art and include 2,6-di-t-butyl-4-methylphenol; 2,6-di-t-butyl-4-methoxymethylphenol; 2,6-dioctadecyl-4-methylphenol; 3,5-di-t-butyl-4-hydroxyanisole; 2,5-di-t-butyl-4-hydroxyanisole; 4-(hydroxymethyl)-2,6-di-t-butylphenol; 4,4'-methylenebis(2,6-di-t-butylphenol); 2,2'-ethylidenebis(4,6-di-t-butylphenol); 4,4'-thiobis(2-methyl-6-t-butylphenol); tetrakis(methylene 3-(3,5-di-t-butyl-4-hydroxyphenyl)propionate)methane: 1,3,5-tris(3,5-di-t-butyl-4-hydroxybenzyl)isocyanurate: 0,0,-di-n-octadecy((3,5-di-t-butyl-4-hydroxybenzyl)phosphonate; octadecyl 3-(3,5-dit-butyl-4-hydroxyphenyl)-propionate; 2,2'-oxamidobisethyl 3-(3,5-di-t-butyl-4-hydroxyphenyl)propionate; calcium bis(0-ethyl(3,5-di-t-butyl-4-hydroxybenzyl)phosphonate) and mixtures thereof. A particularly preferred phenolic antioxidant is 1,3,5-trimethyl-2,4,6-tris(3,5-di-t-butyl-4hydroxybenzyl)benzene which is available from Ethyl Corporation as 10 Ethanox ® 330 Antioxidant.

When utilized, the phenolic antioxidants are preferably present with the aromatic fluorophosphites in an amount in the range of from about 0.005 to about 3.0 percent by weight based on the weight of the total composition.

The following examples are presented to illustrate certain specific embodiments of the invention, but are not intended to be construed so as to be restrictive of the spirit and scope thereof.

EXAMPLE 1

Preparation of bis(2,6di-t-butylphenvl) fluorophosphite

Under an atmosphere of nitrogen, 10.1 grams of bis(2,6-di-t-butylphenyl) chlorophosphite, 2.4 grams of anhydrous potassium fluoride and 100 ml of anhydrous tetrahydrofuran were combined and heated to reflux for 17 hours. Next, an additional 1.0 grams of anhydrous potassium fluoride was added to the mixture. The mixture was heated at reflux for a total of 44 hours and allowed to cool. The resulting slurry was filtered and the filtrate was concentrated under vacuum. The crude product was dissolved in n-heptane and filtered through basic alumina, eluting with n-heptane. The early fractions containing the least polar product were concentrated to 3.6 grams of pale oil. The oil was purified by chromatography on basic alumina, eluting with n-heptane, to yield 1.8 grams of clear oil which solidified to a white solid upon standing.

Spectral analysis (H-NMR, P-NMR, F-NM, mass spectrometry (MS)) confirmed the identity of the which solid as bis(2,6-di-t-butylphenyl) fluorophosphite:

EXAMPLE 2

Preparation of bis(2,6-di-t-butyl-4-(2-carbooctadecyloxyethyl)phenyl) fluorophosphite Under a nitrogen atmosphere, 20 grams of bis(2,6-di-t-butyl-4-(2-carbooctadecyloxyethyl)phenyl chlorophosphite (75 weight percent purity), 3.0 grams of potassium fluoride, and 100 ml of anhydrous tetrahydrofuran were combined and heated to reflux temperature. After heating the mixture for 40 hours at reflux temperature, the mixture was allowed to cool and was subsequently filtered. The filtrate was concentrated to 19.4 grams of white solids. By quantitative P-NMR, the conversion was about 90% and the yield was 86% of bis(2,6-di-t-butyl-4-(2-carbooctadecyloxyethyl)phenyl fluorophosphite.

A sample of the crude product was purified by chromatography for analysis and polymer testing. The spectral analysis (H-NMR, P-NMR and F-NMR) confirmed the identity of the product as bis(2,6-di-t-butyl-4-(2-carbooctadecyloxyethyl)phenyl fluorophosphite.

EXAMPLE 3

Preparation of 2,2'-ethylidenebis(4,6-di-t-butylphenyl) fluorophosphite

Under a nitrogen atmosphere, 117 ml of phosphorus trichloride and 1.3 l of toluene were combined and the admixture was cooled to 5.C. A solution of 573 grams of 2,2'-ethylidenebis(4,6-di-t-butylphenol), 375 ml of triethylamine, and 2.0 l of toluene was added dropwise to the admixture over a period of 6 hours. The reaction mixture was maintained below a temperature of 10° C. during the addition. Next, the reaction mixture was allowed to warm to ambient temperature. After 1 hour at ambient temperature, 135 grams of antimony trifluoride was added to the mixture to form a slurry. Next, the slurry was warmed to 85.C over a period of 1 hour and maintained at this temperature for 4 hours. The crude reaction product comprised a pale green organic layer over a thick green oil. The pale green organic layer was decanted from the oil. The organic layer was filtered through 165 grams of silica gel 60. The filter cake was then washed with toluene. The clear colorless filtrates were concentrated under vacuum to 617 grams of white solids. By quantitative P-NMR, the solids were determined to be a 4:1 mixture of the two possible diasteriomers of 2,2'-ethylidenebis(4,6-di-t-butylphenyl) fluorophosphite. An analysis by H-NMR, P-NMR, F-NMR and MS was consistent with these structures.

EXAMPLE 4

Preparation of bis(2,4-di-t-butylohenyl) fluorophosphite

Under a nitrogen atmosphere, 6 ml of phosphorus trichloride and 100 ml of anhydrous tetrahydrofuran were combined and the admixture was cooled below 10.C. A solution of 28.7 grams of 2,4-di-t-butylphenol, 20 ml of triethylamine, and 150 ml of anhydrous tetrahydrofuran was added dropwise to the admixture over a period of 80 minutes. The resulting slurry was allowed to warm to ambient temperature. After 2 hours at ambient temperature, 8 grams of antimony trifluoride was added to the slurry. The slurry was then heated to reflux temperature and maintained at this temperature for 1 hour. The slurry was allowed to cool and then filtered through basic aluminum oxide. The filter cake was washed with toluene. The filtrates were concentrated under vacuum to 30.8 grams of a pale yellow oil. A 27 gram portion of the crude product was dissolved in 150 ml of n-heptane and filtered to remove insoluble materials. The filtrate was concentrated to 25 grams of a pale yellow oil. The oil was next stirred with 100 ml of acetonitrile. The white solid which was formed was collected by filtration to yield 17.5 grams of bis(2,4-di-t-butylphenyl) fluorophosphite. The H-NMR, P-NMR, F-NMR and MS of the solid were consistent with this structure.

EXAMPLE 5

Preparation of 4,4'-methylenebis(3,5-di-tert-butylphenyl) tetrafluorodiphosphite.

In a reaction vessel under nitrogen was placed 10.7 grams of 4,4'-methylenebis(2,6-di-tert-butylphenol), 4.4 ml of $PCl_3$,7 ml of triethylamine and 100 ml of toluene. The mixture was heated at 50° C. with stirring for 5.5 hours. It was then heated to 80° C. and held at 80° C. for 36 hours. Then 7.2 grams of $SbF_3$ was added and the mixture stirred 4.5 hours at 80° C. and then cooled. Two phases forced. The upper yellow liquid phase was decanted and filtered through silica gel and the filtrate was evaporated to give 11.4 grams residue which solidified to a yellow waxy solid. The crude product was recrystallized from acetonitrile to obtain a white solid (mp. 125–126° C.). The H-NMR, p-NMR were consistent With the target tetrafluorodiphosphite.

EXAMPLE 6

Preparation of 2,2-bis(4,6-di-tert-butylphenyl) fluorophosphite

Under a nitrogen atmosphere a solution of 8.2 grams of 4,4',6,6,-tetra-tert-butyl-2,2'biphenyl and 5.9 ml of triethylamine in 25 ml of toluene was added to a cooled (5° C.) solution of 1.8 ml of $PCl_3$ in 20 ml of toluene over a 1.25 hour period. At the end of the addition, the slurry was stirred 15 minutes and the mixture then warmed to ambient temperature. After stirring overnight, 2.0 grams of $SbF_3$ was added. The resulting slurry was heated to and maintained at 85° C. for 6.5 hours. After cooling, the toluene layer was decanted from the black solid residue and filtered through Celite. The filtrate was evaporated to give about 9 grams of a yellow oil. The yellow oil was washed with acetonitrile and purified by column chromatography in a n-heptane solvent. The product recovered from the eluant was a white solid with a m.p. of 188° C. The P-NMR showed a 1300 Hz doublet at 132.4 ppm (from $H_3PO_4$, $CDCl_3$) which confirmed the identify of the product a the target compound.

| Code for Aromatic Fluorophosphites Used in Examples 7-9 | |
|---|---|
| Chemical Code | Description |
| P-1 | bis(2,6-di-t-butylphenyl) fluorophosphite |
| P-2 | bis(2,4-di-t-butylphenyl) fluorophosphite |
| P-3 | 2,2'-ethylidenebis(4,6-di-t-butylphenyl) fluorophosphite |
| P-4 | bis(2,6-di-t-butyl-4-(2-carboocta-decyloxyethyl)phenyl) fluorophosphite |

EXAMPLE 7

In order to demonstrate the effectiveness of the aromatic fluorophosphite of the present invention as processing stabilizers, bis(2,6-di-t-butyl-4-(2-carbooctadecyloxyethyl)phenyl) fluorophosphite (P-4) and 1,3,5-trimethyl-2,4,6-tris(3,5-di-t-butyl-4-hydroxybenzyl)benzene (Ethanox® 330 Antioxidant) were incorporated into polypropylene powder in accordance with the following procedure. The P-4 and Ethanox® 330 Antioxidant were dissolved in a small amount of methylene chloride and mixed with 50 grams of polypropylene powder (Profax® 6501 polypropylene from Hercules). The mixture was then dry blended with 450g of polypropylene in a nitrogen atmosphere. In some of the formulations, 1000 ppm of calcium stearate (Mallinckrodt RSN 248D) was utilized as an acid neutralizer and lubricating agent. The blended material was extruded under nitrogen on a twin screw mixer (Brabender, 30 rpm) with the temperature profile: zone one 150° C., zone two and zone three—245° C. Then, multiple extrusions were run on the pellets on a single screw extruder (Brabender L/D 24:1) at 550° F. The stock temperature was 265° C. and the screw speed was 30 rpm in an air atmosphere. The extruded strand was cooled by passing it through a room temperature (24–29° C.) water bath. Water carryover was minimized by an air knife that blew the excess water from the strand before it entered the pelletizer. The melt flow index (MFI) was determined with a Tinium Olsen Extrusion Plastometer according to ASTM Method D-1238 Condition L (230° C.-2160 g load). Using the same samples, a 60 mil sheet was pressed out at 375° F. and the color was determined with a Hunterlab Optical Sensor Model D25.

The results of these tests are shown in Table I.

TABLE I

| Test No. | Antioxidant | Wt. % | Melt Flow Index Extrusion Pass No. | | | Yellowness Index Extrusion Pass No. | | |
|---|---|---|---|---|---|---|---|---|
| | | | 1 | 2 | 3 | 1 | 2 | 3 |
| 1 | None | | 13.8 | 26.9 | — | 5.0 | 6.2 | — |
| 2 | Ethanox 330 | 0.05 | 6.7 | 9.4 | 12.6 | 7.2 | — | 9.6 |
| 3 | P-4 | 0.05 | 6.7 | 9.2 | 12.6 | 5.6 | — | 7.9 |
| | Ethanox 330 | 0.05 | | | | | | |
| 4 | Ethanox 330 | 0.05 | 8.9 | 13.2 | 18.8 | 4.5 | — | 6.1 |
| | calcium stearate | 0.10 | | | | | | |
| 5 | Ethanox 330 | 0.05 | 7.9 | 11.5 | 16.2 | 4.5 | — | 6.5 |
| | P-4 | 0.05 | | | | | | |
| | calcium stearate | 0.10 | | | | | | |

These results of these tests show P-4 was effective in suppressing color when used with Ethanox® 330 Antioxidant and reducing the degradation of polypropylene when used with Ethanox® 330 Antioxidant and calcium stearate.

EXAMPLE 8

A series of tests was performed in the same manner as Example 7 to measure Melt Flow Index except that aromatic fluorophosphites, designated as P-2 and P-3, and a different batch of Profax 6501 polypropylene were utilized. In addition, calcium stearate and Ethanox® 330 Antioxidant were used in all tests.

The results of these tests are shown in Table II.

TABLE II

| Test No. | Antioxidant | Wt. % | Melt Flow Index Extrusion Pass No. | | |
|---|---|---|---|---|---|
| | | | 1 | 3 | 5 |
| 1 | Ethanox 330 | 0.05 | 8 | 18 | — |
| | Calcium stearate | 0.10 | | | |
| 2 | P-2 | 0.050 | 5.4 | 9.5 | 15.4 |
| | Ethanox 330 | 0.050 | | | |
| | Calcium stearate | 0.100 | | | |
| 3 | P-3 | 0.050 | 5.5 | 9.3 | 15.1 |

TABLE II-continued

| Test No. | Antioxidant | Wt. % | Melt Flow Index Extrusion Pass No. | | |
|---|---|---|---|---|---|
| | | | 1 | 3 | 5 |
| | Ethanox 330 | 0.050 | | | |
| | Calcium stearate | 0.100 | | | |

The results of these tests demonstrate that the P-2 and P-'aromatic fluorophosphites were effective in reducing the degradation of polypropylene.

EXAMPLE 2

A series of tests were performed in the same manner as Example 8 except that an aromatic fluorophosphite, designated P-1, and a different batch of Profax 6501 polypropylene were utilized and, the multiple extrusions were run at 500° F.

The results of these tests are shown in Table III.

TABLE III

| Test No. | Antioxidant | Wt. % | Melt Flow Index Extrusion Pass No. | | |
|---|---|---|---|---|---|
| | | | 1 | 3 | 5 |
| 1 | Ethanox 330 | 0.05 | 3.4 | 6.2 | 9.6 |
| | Calcium stearate | 0.10 | | | |
| 2 | Ethanox 330 | 0.05 | 2.4 | 3.8 | 5.5 |
| | Calcium stearate | 0.10 | | | |
| | P-1 | 0.05 | | | |

The results of these tests demonstrate that P-1 aromatic fluorophosphite was effective in reducing the degradation of polypropylene.

EXAMPLE 10

The hydrolytic stabilities of the fluorophosphites listed were determined by dissolving 100 mg of the fluorophosphite in a mixture of 2 ml of tetrahydrofuran, 0.2 ml of water and 0.3 ml of $d^8$-tetrahydrofuran (deuteraed THF). The mixtures were stirred at 76° F. and were monitored by P-NMR.

The results of these tests are set forth in Table IV.

TABLE IV

| SAMPLE | % HYDROLYSIS AFTER 2 WEEKS |
|---|---|
| P-1 | 0 |
| P-2 | 0 |
| P-3 | <1 |

The results of these tests show the resistance of the fluorophosphites to hydrolysis over extended periods of time, i.e., 2 weeks.

The invention is not limited to the above-described specific embodiments thereof; it must be understood, therefore, that the detail involved in the descriptions of the specific embodiments is presented for the purpose of illustration only, and that reasonable variations, which will be apparent to those skilled in the art, can be made in tis invention without departing from the spirit and scope thereof.

What is claimed:

1. An aromatic fluorophosphorus compound suitable for use as an antioxidant said compound being selected from fluorophosphorus compounds having the structure:

(RO—) P (—F)$_2$      Formula V wherein R is an substituted aryl group wherein the substituents are tert-alkyl groups:

(R'O—)$_2$P—F      Formula VI wherein R' is a substituted aryl group wherein the substituents are selected from sec-alkyl, tert-alkyl, aralkyl, cycloalkyl, hydroxy, alkoxy, aryloxy, halo, acyloxy, and alkoxy carbonylalkyl:

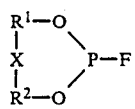

Formula II wherein $R^1$ and $R^2$ are substituted or unsubstituted aryl groups wherein the substituent are selected from alkyl, aryl, aralkyl, cycloalkyl, hydroxy, alkoxy, aryloxy, and halo: and X is selected from the group consisting of a single bond connecting $R^1$ and $R^2$ and divalent bridging groups selected from divalent aliphatic hydrocarbon groups containing 1–12 carbon atoms, —O— and —S$_q$— wherein q is an integer from 1 to 3:

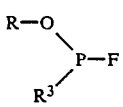

Formula III wherein R is a substituted or unsubstituted aryl group wherein the substituents are selected from alkyl, aryl, aralkyl, cycloalkyl, hydroxy, alkoxy, aryloxy, halo, alkoxycarbonyl, alkoxycarbonylalkyl and acyloxy, and $R^3$ is selected from the group consisting of alkyl, cycloalkyl, aralkyl, aryl, substituted aryl, alkoxy, cycloalkoxy and aralkoxy; and

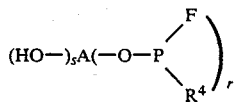

Formula IV wherein A is a mono- or poly-nuclear aromatic group, $R^4$ is independently selected from fluorine, aryloxy, alkylaryloxy, alkoxy and polyalkoxy, r is an integer from 1 to 4, s is an integer from 0 to 3 and (r+s) equals the valence of A.

2. A compound of claim 1 namely bis(2,6-di-tertbutylphenyl) fluorophosphite.

3. A compound of claim 1 namely: bis(2,4-di-tert-butylphenyl) fluorophosphite.

4. A compound of claim 1 namely bis(4-octadecyloxycarbonylethyl-2,6-di-tert-butylphenyl) fluorophosphite.

5. A compound of claim 1 namely: 2,2'-ethylidenebis(4,6-di-tert-butylphenyl) fluorophosphite.

6. A compound of claim 1 namely: bis(difluorophosphite ester) of 4,4'-methylenebis(2,6-di-tert-butylphenol).

7. A compound of claim 1 namely: 2,2'-bis(4,6-di-tert-butylphenyl) fluorophosphite.

8. Organic material normally susceptible to gradual oxidative degradation when in contact with oxygen, said organic material containing an antioxidant amount of an aromatic fluorophosphorus compound, said compound being characterized by having at least one benzene group bonded through oxygen to a trivalent phosphorus atom and at least one fluorine atom bonded to said phosphorus atom.

9. An organic composition of claim 8 wherein said fluorophosphorus compound is selected from the group consisting of compounds having the structures;

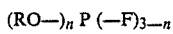   Formula I wherein R is a substituted or unsubstituted aryl group wherein the substituents are selected from alkyl, aryl, aralkyl, cycloalkyl, hydroxy, alkoxy, aryloxy, halo, alkoxycarbonyl, alkoxycarbonylalkyl and acyloxy and n is 1 or 2,

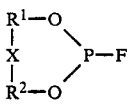   Formula II wherein $R^1$ and $R^2$ are substituted or unsubstituted aryl groups wherein the substituents are selected from alkyl, aryl, aralkyl, cycloalkyl, hydroxy, alkoxy, aryloxy and halo, and X is selected rom the group consisting of a single bond connecting $R^1$ and $R^2$ and divalent bridging groups selected from divalent aliphatic hydrocarbons containing 1–12 carbon atoms, —O— and —$S_q$— wherein q is an integer from 1 to 3;

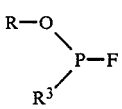   Formula III wherein R is as previously defined for Formula I and $R_3$ is selected from the group consisting of alkyl, cycloalkyl, aralkyl, aryl, substituted aryl, alkoxy, cycloalkoxy, aryloxy and aralkoxy; and

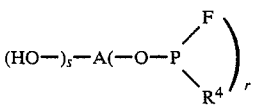   Formula IV wherein A is a mono or polynuclear aromatic group, $R^4$ is independently selected from fluorine, aryloxy, alkaryloxy, alkoxy and polyalkoxy and r is an integer from 1 to 4, s is an integer from 0 to 3 and (r+s) equals the valence of A.

10. A composition of claim 8 wherein said organic material is a polymer of an olefinically unsaturated monomer.

11. A composition of claim 9 wherein said organic material is a polymer of an olefinically unsaturated monomer.

12. A composition of claim 11 wherein said compound has Formula I.

13. A composition of claim 12 wherein n is 2 and said substituents are selected from alkyls having 1-20 carbon atoms, aryls having 6-12 carbon atoms, aralkyls having 7-12 carbon atoms, cycloalkyls having 5-8 carbon atoms, hydroxy, alkoxy having 1-12 carbon atoms, aryloxy having 6-12 carbon atoms, halo, alkoxycarbonylalkyl having 1-20 carbon atoms in its alkoxy moiety and 1-3 carbon atoms in its alkyl moiety, alkoxycarbonyl having 1—20 carbon atoms in its alkoxy moiety and acyloxy having 1-4 carbon atoms.

14. A composition of claim 13 wherein said substituents are selected from alkyl having 1-20 carbon atoms and alkoxy carbonylalkyl having 1-20 carbon atoms in its alkoxy moiety and 4 1-3 carbon atoms in its alkyl moiety.

15. A composition of claim 14 wherein said fluorophosphite compound is bis(2,6-di-tert-butylphenyl) fluorophosphite.

16. A composition of claim 14 wherein said fluorophosphite is bis(2,4-di-tert-butylphenyl) fluorophosphite.

17. A composition of claim 14 wherein said fluorophosphite compound is bis(4-octadecyloxycarbonylethyl-2,6-di-tert-butylphenyl) fluorophosphite.

18. A composition of claim 12 wherein n is 1.

19. A composition of claim 9 wherein said fluorophosphite compound has Formula II wherein said substituents are selected from alkyl having 1-20 carbon atoms, aryl having 6-12 carbon atoms, aralkyl having 7-12 carbon atoms, cycloalkyl having 5-8 carbon atoms, hydroxy, alkoxy having 1-12 carbon toms, aryloxy having 6-12 carbon atoms and halo, and X is selected from the group consisting of a single bond connecting $R^1$ and $R^2$ and divalent bridging groups selected from divalent aliphatic hydrocarbon groups containing 1-12 carbon atoms, —O— and —$S_q$— wherein q is an integer from 1-3.

20. A composition of claim 19 wherein said substituent groups are alkyls containing 1-20 carbon atoms.

21. A composition of claim 20 wherein said fluorophosphorus compound is 2,2'-ethylidenebis(4,6-di-tert-butylphenyl) fluorophosphite.

22. A composition of claim 20 wherein said fluorophosphorus compound is 2,2'-methylenebis (4-methyl-6-tert-butylphenyl) fluorophosphite.

23. A composition of claim 20 wherein said fluorophosphite compound is22,2,-bis(4,6-di-tert-butylphenyl) fluorophosphite.

24. A composition of claim 9 wherein said fluorophosphorus compound has Formula III wherein said substituents are selected from alkyls having 1-20 carbon atoms, aryls having 6-12 carbon atoms, aralkyls having 7-12 carbon atoms, cycloalkyls having 5-8 carbon atoms, hydroxy, alkoxy having 1-12 carbon atoms, aryloxy having 6-12 carbon atoms, halo, alkoxycarbonylalkyl having 1-20 carbon atoms in its alkoxy moiety and 1-3 carbon atoms in its alkyl moiety, alkoxycarbonyl having 1-20 carbon atoms in its alkoxy moiety and acyloxy having 1-4 carbon atoms, and $R^3$ is selected from alkyl having 1-20 carbon atoms, cycloalkyl having 5-8 carbon atoms and aralkyls having 7-12 carbon atoms which are bonded through oxyqen to phosphorus and aryls having 6-12 carbon atoms, alkyl having 1-20 carbon atoms, cycloalkyls having 5-8 carbon atoms and aralkyls having 7-12 carbon atoms which are bonded directly to said phosphorus.

25. A composition of claim 9 wherein said fluorophosphorus compound has Formula IV.

26. A composition of claim 25 wherein A has a structure selected from:

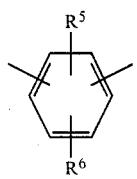   Structure IV (i)

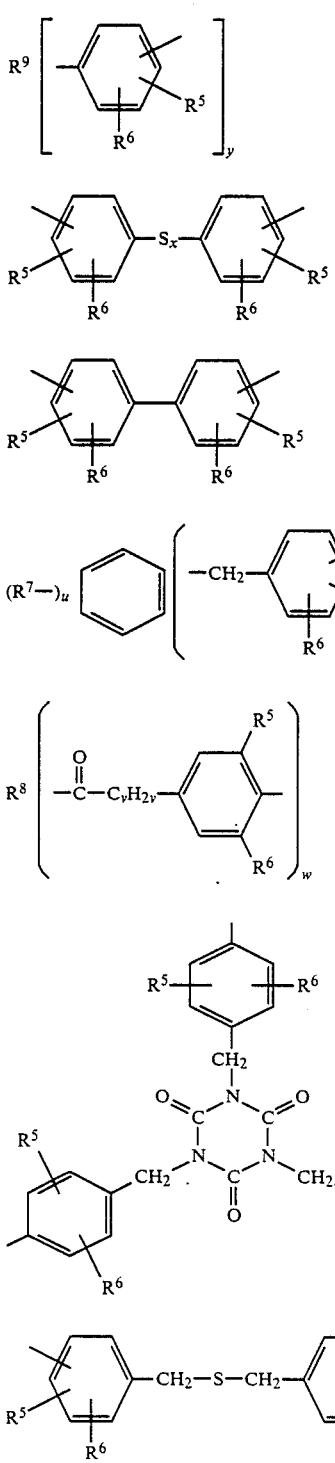

wherein $R^5$ and $R^6$ are hydrogen or alkyl having 1-12 carbon atoms, y is an integer from 2 to 3, x is an integer from 1 to 3, t is an integer from 2 to 3, u is an integer from 0 to 4, (t+u) equals 2 to 6, w is an integer from 1 to 4, $R^7$ is hydrogen or an alkyl having 1 to 6 carbon atoms, $R^8$ is an aliphatic hydrocarbon radical having 1–30 carbon atoms and having valence w, v is an integer from 0 to 4, $R^9$ is an aliphatic hydrocarbon radical having 1 to 6 carbon atoms and having valence y.

27. A composition of claim 26 wherein said fluorophosphorus compound is 2,5-di-tert-butyl-1,4-phenylene bis (difluorophosphite).

28. A composition of claim 26 wherein said fluorophosphorus compound is 4,4'-methylenebis(2,6-di-tert-butylphenyl) bis(difluorophosphite).

29. A composition of claim 26 wherein said fluorophosphite compound is the tris(difluorophosphite ester) of 1,3,5-tris(3,5-di-tert-butyl-4-hydroxybenzyl)-2,4,6-trimethyl benzene.

30. A composition of claim 26 wherein said fluorophosphorus compound is the tetrakis(difluorophosphite ester) of tetrakis(methylene 3-(3,5-di-tert-butyl-4-hydroxyphenyl) propionate)methane.

31. A composition of claim 26 wherein said fluorophosphite compound is difluorophosphite ester of octadecyl 3-(3,5-di-tert-butylhydroxyphenyl)propioniate.

32. An organic composition of claim 8 further characterized by containing about 0.005–5 wt. percent of a phenolic antioxidant.

33. An organic composition of claim 9 further characterized by containing about 0.005–5 wt. percent of a phenolic antioxidant.

34. An organic composition of claim 12 further characterized by containing about 0.005–5 wt. percent of a phenolic antioxidant.

35. An organic composition of claim 15 further characterized by containing about 0.005–5 wt. percent of a phenolic antioxidant.

36. An organic composition of claim 16 further characterized by containing about 0.005–5 wt. percent of a phenolic antioxidant.

37. An organic composition of claim 17 further characterized by containing about 0.005–5 wt. percent of a phenolic antioxidant.

38. An organic composition of claim 19 further characterized by containing about 0.005–5 wt. percent of a phenolic antioxidant.

39. An organic composition of claim 21 further characterized by containing about 0.005–5 wt. percent of a phenolic antioxidant.

40. An organic composition of claim 39 wherein said phenolic antioxidant is 1,3,5-tris(3,5-di-tert-butyl-b 4-hydroxybenzyl)-2,4,6-trimethylbenzene.

41. An organic composition of claim 39 further characterized by containing about 0.005–5 wt. percent of a phenolic antioxidant.

42. An organic composition of claim 25 further characterized by containing about 0.005–5 wt. percent of a phenolic antioxidant.

* * * * *